United States Patent [19]
Hollis et al.

[11] Patent Number: 5,622,842
[45] Date of Patent: Apr. 22, 1997

[54] DNA ENCODING CANINE IMMUNOGLOBULIN A

[75] Inventors: Gregory F. Hollis, Westfield; Mayur D. Patel, Edison, both of N.J.

[73] Assignee: Merck & Co., Inc., Rahway, N.J.

[21] Appl. No.: 336,891

[22] Filed: Nov. 9, 1994

[51] Int. Cl.$^6$ ............ C12N 15/13; C12N 15/63; C12N 5/10; C07K 16/00

[52] U.S. Cl. ............ 435/69.6; 435/252.3; 435/320.1; 536/23.53; 530/387.1

[58] Field of Search ............ 530/387.1; 536/23.53; 435/320.1, 252.3, 69.6

[56] References Cited

FOREIGN PATENT DOCUMENTS

WO94/21676  9/1994  WIPO.

OTHER PUBLICATIONS

Hieter Nature 294:536–540, 1981.
McCumber and Capra, Mol. Immunol. 16:565–569, 1979.
Wasserman and Capra, Science 200:1159–1661, 1978.
Osborne et al. Genetics 119:925–931, 1988.
Flanagan, Cell 36:681–688, 1984.
Glickman Am J. Vet Res 49:1240–1245, 1988.
Morrison Science 229:1202–1207, 1985.

*Primary Examiner*—Marian C. Knode
*Assistant Examiner*—Nancy A. Johnson
*Attorney, Agent, or Firm*—Christine E. Carty; Jack L. Tribble

[57] ABSTRACT

The present invention relates to DNA molecules encoding a canine IgA and species-specific regions of the canine IgA constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

4 Claims, 5 Drawing Sheets

```
                    10                  30                  50
                    .                   .                   .
  1  AGTGACCTAGCGTGTCATTCTGACCCAGGTCTCGGCATATGAACTGCATGACCTTGGGCT  60

70                  90                 110
                    .                   .                   .
 61  GTCACTGACCATCTCTATGCAGTTTCCTCTAGTGCAAAGAAAAAATAGCCCTCACCCTGC  120

130                 150                 170
                    .                   .                   .
121  CTGTGAGGCCATGTAAGGGGTCCAGACAGCACTGGCCCACCAGCTCACAGAGTGTCCTGT  180

190                 210                 230
                    .                   .                   .
181  GTCACAGAGTCCAAAACCAGCCCCAGTGTGTTCCCGCTGAGCCTCTGCCACCAGGAGTCA  240
        XXSerLysThrSerProSerValPheProLeuSerLeuCysHisGlnGluSer 250                 270                 290
                    .                   .                   .
241  GAAGGGTACGTGGTCATCGGCTGCCTGGTGCAGGGATTCTTCCCACCGGAGCCTGTGAAC  300
     GluGlyTyrValValIleGlyCysLeuValGlnGlyPhePheProProGluProValAsn 310                 330                 350
                    .                   .                   .
301  GTGACCTGGAATGCCGGCAAGGACAGCACATCTGTCAAGAACTTCCCCCCCATGAAGGCT  360
     ValThrTrpAsnAlaGlyLysAspSerThrSerValLysAsnPheProProMetLysAla 370                 390                 410
                    .                   .                   .
361  GCTACCGGAAGCCTATACACCATGAGCAGCCAGTTGACCCTGCCAGCCGCCCAGTGCCCT  420
     AlaThrGlySerLeuTyrThrMetSerSerGlnLeuThrLeuProAlaAlaGlnCysPro 430                 450                 470
                    .                   .                   .
421  GATGACTCGTCTGTGAAATGCCAAGTGCAGCATGCTTCCAGCCCCAGCAAGGCAGTGTCT  480
     AspAspSerSerValLysCysGlnValGlnHisAlaSerSerProSerLysAlaValSer 490                 510                 530
                    .                   .                   .
481  GTGCCCTGCAAAGGTCAGAGGGCAGGCTGGGGAGGGGCAGGGGCCCCACATCCTCACTCT  540
```

FIG.1A

```
                    550                  570                  590
      541  GACCCTCCACTTGGAGTTCTGGCCCCAAGGACACTCCACGGGGAGGACAGTGGGCTGCTG  600

610                  630                  650
      601  GGCTGAGCTCCCAGCAAGTGGCCAAGGTGGGGCCTCCATGAAGGACCTGGAGGGTGGCAG  660

670                  690                  710
      661  GGGGCAGGCAGGCAGAGGGTGCACACTGACCTGTTCCAATCTCTCTCTCTCTCTCTCT    720

730                  750                  770
      721  CTCTCTCTGCTCCTGAAGATAACAGTCATCCGTGTCATCCATGTCCCTCGTGCAATGAGC  780
                                  spAsnSerHisProCysHisProCysProSerCysAsnGluP 790                  810                  830
      781  CCCGCCTGTCACTACAGAAGCCAGCCCTCGAGGATCTGCTTTTAGGCTCCAATGCCAGCC  840
           roArgLeuSerLeuGlnLysProAlaLeuGluAspLeuLeuLeuGlySerAsnAlaSerL 850                  870                  890
      841  TCACATGCACACTGAGTGGCCTGAAAGACCCCAAGGGTGCCACCTTCACCTGGAACCCCT  900
           euThrCysThrLeuSerGlyLeuLysAspProLysGlyAlaThrPheThrTrpAsnProS 910                  930                  950
      901  CCAAAGGGAAGGAACCCATCCAGAAGAATCCTGAGCGTGACTCCTGTGGCTGCTACAGTG  960
           erLysGlyLysGluProIleGlnLysAsnProGluArgAspSerCysGlyCysTyrSerV 970                  990                  1010
      961  TGTCCAGTGTCCTACCAGGCTGTGCTGATCCATGGAACCATGGGGACACCTTCTCCTGCA  1020
           alSerSerValLeuProGlyCysAlaAspProTrpAsnHisGlyAspThrPheSerCysT 1030                 1050                 1070
      1021 CAGCCACCCACCCTGAATCCAAGAGCCCGATCACTGTCAGCATCACCAAAACCACAGGTG  1080
           hrAlaThrHisProGluSerLysSerProIleThrValSerIleThrLysThrThrG
```

FIG.1B

```
          1090              1110              1130
1081  GGCCCAGACCCTGCCCGTGAGGCACTGCTTGGCACACAAAAGTTTGTGAGGCAACTCCTA  1140

1150              1170              1190
1141  AGCCTGCTTCCTTCCTCTAGCCCCTGGGCTTGGGTGCTCCCACCCACATTTTACAAAGGG  1200

1210              1230              1250
1201  AAACTGTGGCATGGGGTGCTATGGGGAAGAAGGCTCTTCCCCCACCCCAGATCCCTGACC  1260

1270              1290              1310
1261  TGGCTCTCTGTCCTGCAGAGCACATCCCGCCCCAGGTCCACCTGCTGCCGCCGCCGTCGG  1320
                       luHisIleProProGlnValHisLeuLeuProProProSerG 1330              1350              1370
1321  AAGAGCTGGCCCTCAATGAGCTGGTGACACTGACGTGCTTGGTGAGGGGCTTCAAACCAA  1380
      luGluLeuAlaLeuAsnGluLeuValThrLeuThrCysLeuValArgGlyPheLysProL 1390              1410              1430
1381  AAGATGTGCTCGTACGATGGCTGCAAGGGACCCAGGAGCTACCCCAAGAGAAGTACTTGA  1440
      ysAspValLeuValArgTrpLeuGlnGlyThrGlnGluLeuProGlnGluLysTyrLeuT 1450              1470              1490
1441  CCTGGGAGCCCCTGAAGGAGCCTGACCAGACCAACATGTTTGCCGTGACCAGCATGCTGA  1500
      hrTrpGluProLeuLysGluProAspGlnThrAsnMetPheAlaValThrSerMetLeuA 1510              1530              1550
1501  GGGTGACAGCCGAAGACTGGAAGCAGGGGGAGAAGTTCTCCTGCATGGTGGGCCACGAGG  1560
      rgValThrAlaGluAspTrpLysGlnGlyGluLysPheSerCysMetValGlyHisGluA 1570              1590              1610
1561  CTCTGCCCATGTCCTTCACCCAGAAGACCATCGACCGCCTGGCGGGTAAACCCACCCACG  1620
      laLeuProMetSerPheThrGlnLysThrIleAspArgLeuAlaGlyLysProThrHisV
```

FIG.1C

```
                    1630                1650                1670
                      .                   .                   .
1621  TCAACGTGTCTGTGGTCATGGCAGAGGTGGACGGCATCTGCTACTAAACCGCCCAATCTT  1680
      alAsnValSerValValMetAlaGluValAspGlyIleCysTyr 1690                1710                1730
                      .                   .                   .
1681  CCCTCCCTAAATAAACTCCATGCTTGCCCAAAGCAGCCCCGTGCTTCCATCAGGCCGCCT  1740

1750                1770
                      .                   .
1741  GTCTGTCCATATTCGGGGTCTGTGGCATACTGAGGCAGGGGTAGAGCTC  1789
```

FIG. 1D

| % IDENTITY OF CANINE Igα TO Igα OF OTHER SPECIES | | | | |
|---|---|---|---|---|
| | CH1 | CH2 | CH3 | TOTAL |
| MOUSE Igα DNA | 59 | 73 | 78 | 71 |
| MOUSE Igα PROTEIN | 52 | 67 | 73 | 65 |
| HUMAN Igα 1 DNA | 72 | 74 | 83 | 76 |
| HUMAN Igα 1 PROTEIN | 57 | 70 | 82 | 70 |

FIG.2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1789 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGTGACCTAG  CGTGTCATTC  TGACCCAGGT  CTCGGCATAT  GAACTGCATG  ACCTTGGGCT       60

GTCACTGACC  ATCTCTATGC  AGTTTCCTCT  AGTGCAAAGA  AAAAATAGCC  CTCACCCTGC      120

CTGTGAGGCC  ATGTAAGGGG  TCCAGACAGC  ACTGGCCCAC  CAGCTCACAG  AGTGTCCTGT      180

GTCACAGAGT  CCAAAACCAG  CCCCAGTGTG  TTCCCGCTGA  GCCTCTGCCA  CCAGGAGTCA      240

GAAGGGTACG  TGGTCATCGG  CTGCCTGGTG  CAGGGATTCT  TCCCACCGGA  GCCTGTGAAC      300

GTGACCTGGA  ATGCCGGCAA  GGACAGCACA  TCTGTCAAGA  ACTTCCCCCC  CATGAAGGCT      360

GCTACCGGAA  GCCTATACAC  CATGAGCAGC  CAGTTGACCC  TGCCAGCCGC  CCAGTGCCCT      420

GATGACTCGT  CTGTGAAATG  CCAAGTGCAG  CATGCTTCCA  GCCCCAGCAA  GGCAGTGTCT      480

GTGCCCTGCA  AAGGTCAGAG  GGCAGGCTGG  GGAGGGGCAG  GGGCCCCACA  TCCTCACTCT      540
```

| | | | | | | |
|---|---|---|---|---|---|---|
| GACCCTCCAC | TTGGAGTTCT | GGCCCCAAGG | ACACTCCACG | GGGAGGACAG | TGGGCTGCTG | 600 |
| GGCTGAGCTC | CCAGCAAGTG | GCCAAGGTGG | GGCCTCCATG | AAGGACCTGG | AGGGTGGCAG | 660 |
| GGGCAGGCA | GGCAGAGGGT | GCACACTGAC | CTGTTCCAAT | CTCTCTCTCT | CTCTCTCTCT | 720 |
| CTCTCTCTGC | TCCTGAAGAT | AACAGTCATC | CGTGTCATCC | ATGTCCCTCG | TGCAATGAGC | 780 |
| CCCGCCTGTC | ACTACAGAAG | CCAGCCCTCG | AGGATCTGCT | TTTAGGCTCC | AATGCCAGCC | 840 |
| TCACATGCAC | ACTGAGTGGC | CTGAAAGACC | CCAAGGGTGC | CACCTTCACC | TGGAACCCCT | 900 |
| CCAAAGGGAA | GGAACCCATC | CAGAAGAATC | CTGAGCGTGA | CTCCTGTGGC | TGCTACAGTG | 960 |
| TGTCCAGTGT | CCTACCAGGC | TGTGCTGATC | CATGGAACCA | TGGGGACACC | TTCTCCTGCA | 1020 |
| CAGCCACCCA | CCCTGAATCC | AAGAGCCCGA | TCACTGTCAG | CATCACCAAA | ACCACAGGTG | 1080 |
| GGCCCAGACC | CTGCCCGTGA | GGCACTGCTT | GGCACACAAA | AGTTTGTGAG | GCAACTCCTA | 1140 |
| AGCCTGCTTC | CTTCCTCTAG | CCCCTGGGCT | TGGGTGCTCC | CACCCACATT | TTACAAAGGG | 1200 |
| AAACTGTGGC | ATGGGGTGCT | ATGGGGAAGA | AGGCTCTTCC | CCCACCCCAG | ATCCCTGACC | 1260 |
| TGGCTCTCTG | TCCTGCAGAG | CACATCCCGC | CCAGGTCCA | CCTGCTGCCG | CCGCCGTCGG | 1320 |
| AAGAGCTGGC | CCTCAATGAG | CTGGTGACAC | TGACGTGCTT | GGTGAGGGGC | TTCAAACCAA | 1380 |
| AAGATGTGCT | CGTACGATGG | CTGCAAGGGA | CCCAGGAGCT | ACCCCAAGAG | AAGTACTTGA | 1440 |
| CCTGGGAGCC | CCTGAAGGAG | CCTGACCAGA | CCAACATGTT | TGCCGTGACC | AGCATGCTGA | 1500 |
| GGGTGACAGC | CGAAGACTGG | AAGCAGGGGG | AGAAGTTCTC | CTGCATGGTG | GGCCACGAGG | 1560 |
| CTCTGCCCAT | GTCCTTCACC | CAGAAGACCA | TCGACCGCCT | GGCGGGTAAA | CCCACCCACG | 1620 |
| TCAACGTGTC | TGTGGTCATG | GCAGAGGTGG | ACGGCATCTG | CTACTAAACC | GCCCAATCTT | 1680 |
| CCCTCCCTAA | ATAAACTCCA | TGCTTGCCCA | AAGCAGCCCC | GTGCTTCCAT | CAGGCCGCCT | 1740 |
| GTCTGTCCAT | ATTCGGGGTC | TGTGGCATAC | TGAGGCAGGG | GTAGAGCTC | | 1789 |

( 2 ) INFORMATION FOR SEQ ID NO:2:

( i ) SEQUENCE CHARACTERISTICS:
      ( A ) LENGTH: 343 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:2:

```
Ser  Lys  Thr  Ser  Pro  Ser  Val  Phe  Pro  Leu  Ser  Leu  Cys  His  Gln  Glu
  1              5                  10                      15

Ser  Glu  Gly  Tyr  Val  Val  Ile  Gly  Cys  Leu  Val  Gln  Gly  Phe  Phe  Pro
                  20                  25                      30

Pro  Glu  Pro  Val  Asn  Val  Thr  Trp  Asn  Ala  Gly  Lys  Asp  Ser  Thr  Ser
            35                  40                      45

Val  Lys  Asn  Phe  Pro  Pro  Met  Lys  Ala  Ala  Thr  Gly  Ser  Leu  Tyr  Thr
       50                  55                      60

Met  Ser  Ser  Gln  Leu  Thr  Leu  Pro  Ala  Ala  Gln  Cys  Pro  Asp  Asp  Ser
 65                  70                      75                          80

Ser  Val  Lys  Cys  Gln  Val  Gln  His  Ala  Ser  Ser  Pro  Ser  Lys  Ala  Val
                     85                      90                      95

Ser  Val  Pro  Cys  Lys  Asp  Asn  Ser  His  Pro  Cys  His  Pro  Cys  Pro  Ser
                100                     105                     110

Cys  Asn  Glu  Pro  Arg  Leu  Ser  Leu  Gln  Lys  Pro  Ala  Leu  Glu  Asp  Leu
             115                     120                     125

Leu  Leu  Gly  Ser  Asn  Ala  Ser  Leu  Thr  Cys  Thr  Leu  Ser  Gly  Leu  Lys
```

|     |     |     |     |     | 130 |     |     |     |     | 135 |     |     |     |     | 140 |     |     |     |     |
|---|---|---|---|---|---|---|---|---|---|---|---|---|---|---|---|---|---|---|---|
| Asp | Pro | Lys | Gly | Ala | Thr | Phe | Thr | Trp | Asn | Pro | Ser | Lys | Gly | Lys | Glu |
| 145 |     |     |     |     | 150 |     |     |     |     | 155 |     |     |     |     | 160 |
| Pro | Ile | Gln | Lys | Asn | Pro | Glu | Arg | Asp | Ser | Cys | Gly | Cys | Tyr | Ser | Val |
|     |     |     |     | 165 |     |     |     |     | 170 |     |     |     |     | 175 |     |
| Ser | Ser | Val | Leu | Pro | Gly | Cys | Ala | Asp | Pro | Trp | Asn | His | Gly | Asp | Thr |
|     |     |     | 180 |     |     |     |     | 185 |     |     |     |     | 190 |     |     |
| Phe | Ser | Cys | Thr | Ala | Thr | His | Pro | Glu | Ser | Lys | Ser | Pro | Ile | Thr | Val |
|     |     | 195 |     |     |     |     | 200 |     |     |     |     | 205 |     |     |     |
| Ser | Ile | Thr | Lys | Thr | Thr | Glu | His | Ile | Pro | Pro | Gln | Val | His | Leu | Leu |
|     | 210 |     |     |     |     | 215 |     |     |     |     | 220 |     |     |     |     |
| Pro | Pro | Pro | Ser | Glu | Glu | Leu | Ala | Leu | Asn | Glu | Leu | Val | Thr | Leu | Thr |
| 225 |     |     |     |     | 230 |     |     |     |     | 235 |     |     |     |     | 240 |
| Cys | Leu | Val | Arg | Gly | Phe | Lys | Pro | Lys | Asp | Val | Leu | Val | Arg | Trp | Leu |
|     |     |     |     | 245 |     |     |     |     | 250 |     |     |     | 255 |     |     |
| Gln | Gly | Thr | Gln | Glu | Leu | Pro | Gln | Glu | Lys | Tyr | Leu | Thr | Trp | Glu | Pro |
|     |     |     | 260 |     |     |     |     | 265 |     |     |     |     | 270 |     |     |
| Leu | Lys | Glu | Pro | Asp | Gln | Thr | Asn | Met | Phe | Ala | Val | Thr | Ser | Met | Leu |
|     |     | 275 |     |     |     |     | 280 |     |     |     |     | 285 |     |     |     |
| Arg | Val | Thr | Ala | Glu | Asp | Trp | Lys | Gln | Gly | Glu | Lys | Phe | Ser | Cys | Met |
|     | 290 |     |     |     |     | 295 |     |     |     |     | 300 |     |     |     |     |
| Val | Gly | His | Glu | Ala | Leu | Pro | Met | Ser | Phe | Thr | Gln | Lys | Thr | Ile | Asp |
| 305 |     |     |     |     | 310 |     |     |     |     | 315 |     |     |     |     | 320 |
| Arg | Leu | Ala | Gly | Lys | Pro | Thr | His | Val | Asn | Val | Ser | Val | Val | Met | Ala |
|     |     |     |     | 325 |     |     |     |     | 330 |     |     |     |     | 335 |     |
| Glu | Val | Asp | Gly | Ile | Cys | Tyr |     |     |     |     |     |     |     |     |     |
|     |     |     | 340 |     |     |     |     |     |     |     |     |     |     |     |     |

DNA ENCODING CANINE IMMUNOGLOBULIN A

BACKGROUND OF THE INVENTION

The invention relates to DNA molecules encoding a canine IgA. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

Immunoglobulin (Ig) proteins consist of two identical light (L) chains and two identical heavy (H) chains. Both Ig L and H chains contain an amino-terminal variable region of approximately 110 amino acids that forms the antigen binding domain. The carboxy terminal constant (C) region domains of each chain is defined by two isotypes of IgL chain ( kappa and lambda) and multiple isotypes of IgH chains (mu, delta, gamma, epsilon and alpha which define IgM, IgD, IgG, IgE, and IgA, respectively). The IgH chain C regions contain the effector functions common to antibodies of a given isotype.

Substantial variations in the quantities of specific IgH chain isotypes are observed when different tissue fluids are analyzed. For instance, IgA is the primary Ig isotype in mucosal fluids, but is found at low levels in serum. The preponderance of IgA found at mucosal sites reflects the critical role IgA provides as a first line of defense against pathogens invading epithelial surfaces.

IgA is the principal immunoglobulin of mucosal surfaces where it is secreted as a polymeric antibody complex that contains J chain and secretory component. To fully understand antibody mediated immune responses at mucosal surfaces in a specific species, a knowledge of the Igα constant region gene from that species is required.

Substantial variation in Igα C regions gene copy number among species has been reported. For instance, functional Igα gene copy number differs widely from mouse (one) and human (two) to rabbit. Our studies indicates that only a single Igα gene is present in the canine genome. Unlike other immunoglobulin genes, the hinge region of Igα is not encoded by a separate exon, but rather is fused to the 5' end of the CH2 domain. This organization of hinge and CH2 is conserved in the canine Igα gene. The length of the Igα hinge region has been shown to vary. For instance, the human Igα1 gene has a hinge region of 18 amino acids while the human Igα2 gene hinge region is only 5 amino acids long. The canine Igα gene hinge region is 10 amino acids long, identical in length to the mouse Igα hinge region.

Studies have suggested that the primary interactions between IgA and secretory component reside in the CH2 and CH3 domains of Igα. Secretory component is covalently linked to IgA through disulfide bonds. Cys 311 of the human Iga CH2 domain is responsible for this linkage. Covalent linkage of canine Igα to secretory component may also occur at this position because this cysteine residue is conserved in the canine Igα chain.

For therapeutic purposes, it may be desirable to generate antibodies against the IgA of the target species in order to maximize the affinity of the anti-IgA antibodies. In addition, screening assays aimed at the identification of small molecules which alter IgA mediated responses in the dog can be optimized through the use of canine IgA, the actual target.

Prior to the described invention, it was virtually impossible to design peptides which could be used to produce antibodies of specifically targeted against canine IgA. When IgA sequences from other species are used for this purpose, the resulting antibodies have reduced affinity for the canine IgA and, therefore, reduced efficacy compared with antibodies generated using the described invention. Further, the availability of the cloned canine IgA gene enables large quantities of the canine IgA protein to be produced recombinantly for use in drug development (e.g., small molecule screening, assay development and anti-IgA antibody generation).

The DNA of the present invention may be used to identify regions of the canine IgA which are homologous to those targeted in other species and to predict novel therapeutic targets. Therapeutically interesting portions of the sequence may be expressed in chimeric proteins or used to produce peptides.

The invention also provides a renewable source of canine IgA protein through its expression using recombinant DNA techniques. This provides material for establishing assays to monitor IgA-mediated immune responses.

BRIEF DESCRIPTION OF THE DRAWINGS

FIG. 1 shows the nucleotide(SEQ. ID. NO.:1) and predicted amino acid (SEQ. ID. NO.:2) sequences of canine immunoglobulin A.

FIG. 2 shows a comparison of percent identity of nucleotide and amino acid sequence of canine Igα chain to human and mouse Igα chain.

SUMMARY OF THE INVENTION

The present invention relates to DNA molecules encoding a canine IgA and species-specific regions of the canine IgA constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

DETAILED DESCRIPTION OF THE INVENTION

The present invention relates to DNA molecules encoding a canine IgA and species-specific regions of the canine IgA constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

DNA encoding canine IgA from a particular species of canine may be used to isolate and purify homologues of canine IgA from other canines. To accomplish this, the first canine IgA DNA may be mixed with a sample containing DNA encoding homologues of canine IgA under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alterative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis.

As used herein, a "functional derivative" of canine IgA is a compound that possesses a biological activity (either functional or structural) that is substantially similar to the biological activity of canine IgA. The term "functional derivatives" is intended to include the "fragments," "variants," "degenerate variants," "analogs" and "homologues" or to "chemical derivatives" of canine IgA. The term "fragment" is meant to refer to any polypeptide subset of canine IgA. The term "variant" is meant to refer to a molecule substantially similar in structure and function to either the entire canine IgA molecule or to a fragment thereof. A molecule is "substantially similar" to canine IgA if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire canine IgA molecule or to a fragment thereof.

As used herein, a protein or peptide is "substantially pure" when that protein or peptide has been purified to the extent that it is essentially free of other molecules with which it is associated in nature. The term "substantially pure" is used relative to proteins or peptides with which the peptides of the instant invention are associated in nature, and are not intended to exclude compositions in which the peptide of the invention is admixed with nonproteinous pharmaceutical carriers or vehicles.

As used herein, an amino acid sequence substantially homologous to a referent IgA protein will have at least 70% sequence homology, preferably 80%, and most preferably 90% sequence homology with the amino acid sequence of a referent IgA protein or a peptide thereof. For example, an amino acid sequence is substantially homologous to canine IgA protein if, when aligned with canine lgA protein, at least 70% of its amino acid residues are the same.

As used herein, a DNA sequence substantially homologous to a referent canine IgA protein will have at least 70%, preferably 80%, and most preferably 90% sequence homology with the DNA sequence of a referent canine IgA. Moreover, a DNA sequence substantially homologous to a referent canine IgA protein is characterized by the ability to hybridize to the DNA sequence of a referent canine IgA under standard conditions. Standard hybridization conditions are described in Maniatis, T., et al. (1989) Molecular Cloning, Cold Spring Harbor Laboratory, Cold Spring Harbor, N.Y.

A variety of procedures known in the an may be used to molecularly clone canine IgA DNA. These methods include, but are not limited to, direct functional expression of the canine IgA genes following the construction of a canine IgA-containing cDNA or genomic DNA libraries in an appropriate expression vector system. Another method is to screen canine IgA-containing cDNA or genomic DNA library constructed in a bacteriophage or plasmid shuttle vector with a labeled oligonucleotide probe designed from the amino acid sequence of the canine IgA subunits. An additional method consists of screening a canine IgA-containing cDNA or genomic DNA library constructed in a bacteriophage or plasmid shuttle vector with a partial DNA encoding the canine IgA. This partial DNA is obtained by the specific PCR amplification of canine IgA DNA fragments through the design of degenerate oligonucleotide primers from the amino acid sequence of the purified canine IgA. Another method is to isolate RNA from canine IgA-producing cells and translate the RNA into protein via an in vitro or an in vivo translation system. The translation of the RNA into a peptide or a protein will result in the production of at least a portion of the canine IgA protein which can be identified by, for example, by the activity of canine IgA protein or by immunological reactivity with an anti-canine IgA antibody. In this method, pools of RNA isolated from canine IgA-producing cells can be analyzed for the presence of an RNA which encodes at least a portion of the canine IgA protein. Further fractionation of the RNA pool can be done to purify the canine IgA RNA from non-canine IgA RNA. The peptide or protein produced by this method may be analyzed to provide amino acid sequences which in turn are used to provide primers for production of canine IgA cDNA, or the RNA used for translation can be analyzed to provide nucleotide sequences encoding canine IgA and produce probes for the production of canine IgA cDNA. These methods are known in the art and can be found in, for example, Sambrook, J., Fritsch, E.F., Maniatis, T. in Molecular Cloning: A Laboratory Manual, Second Edition, Cold Spring Harbor Laboratory Press, Cold Spring Harbor, N.Y. 1989.

Other types of libraries, as well as libraries constructed from other cells or cell types, may be useful for isolating canine IgA-encoding DNA. Other types of libraries include, but are not limited to, cDNA libraries derived from other canines or cell lines derived from other canines, and genomic DNA libraries.

Preparation of cDNA libraries can be performed by standard techniques. Well-known cDNA library construction techniques can be found in, for example, Sambrook, J., et al., supra.

DNA encoding canine IgA may also be isolated from a suitable genomic DNA library. Construction of genomic DNA libraries can be performed by standard techniques. Well-known genomic DNA library construction techniques can be found in Sambrook, J., et al, supra In order to clone the canine IgA gene by the above methods, knowledge of the amino acid sequence of canine IgA may be necessary. To accomplish this, canine IgA protein may be purified and partial amino acid sequence determined by manual sequencing or automated sequenators. It is not necessary to determine the entire amino acid sequence, but the linear sequence of two regions of 6 to 8 amino acids from the protein is determined for the production of primers for PCR amplification of a partial canine IgA DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the canine IgA sequence but will be capable of hybridizing to canine IgA DNA even in the presence of DNA oligonucleotides with mismatches under appropriate conditions. Under alternate conditions, the mismatched DNA oligonucleotides may still sufficiently hybridize to the canine IgA DNA to permit identification and isolation of canine IgA encoding DNA.

Purified biologically active canine IgA may have several different physical forms. Canine IgA may exist as a full-length nascent or unprocessed polypeptide, or as partially processed polypeptides or combinations of processed polypeptides. The full-length nascent canine IgA polypeptide may be postranslationally modified by specific proteolytic cleavage events which result in the formation of fragments of the full length nascent polypeptide.

Canine IgA in substantially pure form derived from natural sources or from recombinant host cells according to the purification processes described herein, is found to be a polypeptide encoded by a single mRNA.

The cloned canine IgA DNA obtained through the methods described herein may be recombinantly expressed by molecular cloning into an expression vector containing a suitable promoter and other appropriate transcription regulatory elements, and transferred into prokaryotic or eukaryotic host cells to produce recombinant canine IgA. Techniques for such manipulations are fully described in Sambrook, J., et al., supra,.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant canine IgA in mammalian cells. Commercially available mammalian expression vectors which may be suitable for recombinant canine IgA expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant canine IgA in bacterial cells. Commercially available bacterial expression vectors which may be suitable for recombinant canine IgA expression include, but are not limited to pET11a (Novagen), lambda gt11 (Invitrogen), pcDNAII (Invitrogen), pKK223-3 (Pharmacia).

A variety of fungal cell expression vectors may be used to express recombinant canine IgA in fungal cells. Commercially available fungal cell expression vectors which may be suitable for recombinant canine IgA expression include but are not limited to pYES2 (Invitrogen), Pichia expression vector (Invitrogen).

A variety of insect cell expression vectors may be used to express recombinant canine IgA in insect cells. Commercially available insect cell expression vectors which may be suitable for recombinant expression of canine IgA include but are not limited to pBlue Bac III (Invitrogen).

An expression vector containing DNA encoding canine IgA may be used for expression of canine IgA in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK-) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce canine IgA protein. Identification of canine IgA expressing host cell clones may be done by several means, including but not limited to immunological reactivity with anti-canine IgA antibodies, and the presence of host cell-associated canine IgA activity, such as canine IgA-specific ligand binding or signal transduction defined as a response mediated by the interaction of canine IgA-specific ligands at the receptor.

Expression of canine IgA DNA may also be performed using in vitro produced synthetic mRNA or native mRNA. Synthetic mRNA or mRNA isolated from canine IgA producing cells can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Host cell transfectants and microinjected oocytes may be assayed for both the levels of canine IgA receptor activity and levels of canine IgA protein by a variety of methods.

Following expression of canine IgA in a recombinant host cell, canine IgA protein may be recovered to provide canine IgA in purified form. Several canine IgA purification procedures are available and suitable for use. As described herein, recombinant canine IgA may be purified from cell lysates and extracts by various combinations of, or individual application of salt fractionation, ion exchange chromatography, size exclusion chromatography, hydroxylapatite adsorption chromatography and hydrophobic interaction chromatography.

In addition, recombinant canine IgA can be separated from other cellular proteins by use of an immunoaffinity column made with monoclonal or polyclonal antibodies specific for full length nascent canine IgA, or polypeptide fragments of canine IgA.

Monospecific antibodies to canine IgA are purified from mammalian antisera containing antibodies reactive against canine IgA or are prepared as monoclonal antibodies reactive with canine IgA using the technique of Kohler and Milstein, *Nature* 256, 495–497 (1975). Monospecific antibody as used herein is defined as a single antibody species or multiple antibody species with homogenous binding characteristics for canine IgA. Homogenous binding as used herein refers to the ability of the antibody species to bind to a specific antigen or epitope, such as those associated with the canine IgA, as described above. Canine IgA specific antibodies are raised by immunizing animals such as mice, rats, guinea pigs, rabbits, goats, horses and the like, with rabbits being preferred, with an appropriate concentration of canine IgA either with or without an immune adjuvant.

Monoclonal antibodies (mAb) reactive with canine IgA are prepared by immunizing inbred mice, preferably Balb/c, with canine IgA. The mice are immunized by the IP or SC route with about 0.1 µg to about 10 µg, preferably about 1 µg, of canine IgA in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 µg of canine IgA in a buffer solution such as phosphate buffered saline by the intravenous (IV) route. Lymphocytes, from antibody positive mice, preferably splenic lymphocytes, are obtained by removing spleens from immununized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's Modified Eagles Medium (DMEM) by procedures known in the art. Supermatant fluids are collected from growth positive wells on about days 14, 18, and 21 and are screened for antibody production by an immunoassay such as solid phase immunoradioassay (SPIRA) using canine IgA as the antigen. The culture fluids are also tested in the Ouchterlony precipitation assay to determine the isotype of the mAb. Hybridoma cells from antibody positive wells are cloned by a technique such as the soft agar technique of MacPherson, *Soft Agar Techniques*, in *Tissue Culture Methods and Applications*, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-canine IgA mAb is carded out by growing the hydridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of canine IgA in body fluids or tissue and cell extracts.

The above described methods for producing monospecific antibodies may be utilized to produce antibodies specific for canine IgA polypeptide fragments, or full-length nascent canine IgA polypeptide The present invention is also directed to methods for screening for compounds which modulate the expression of DNA or RNA encoding canine IgA as well as the function of canine IgA protein in vivo. Compounds which modulate these activities may be DNA, RNA, peptides, proteins, or non-proteinaceous organic molecules. Compounds may modulate by increasing or attenuating the expression of DNA or RNA encoding canine IgA, or the function of canine IgA protein. Compounds that modulate the expression of DNA or RNA encoding canine IgA or the function of canine IgA protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing canine IgA DNA, antibodies to canine IgA, or canine IgA protein may be prepared. Such kits are used to detect DNA which hybridizes to canine IgA DNA or to detect the presence of canine IgA protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of canine IgA DNA, canine IgA RNA or canine IgA protein. The recombinant proteins, DNA molecules, RNA molecules and antibodies lend themselves to the formulation of kits suitable for the detection and typing of canine IgA. Such a kit would comprise a compartmentalized carder suitable to hold in close confinement at least one container. The carder would further comprise reagents such as recombinant canine IgA protein or anti-canine IgA antibodies suitable for detecting canine IgA. The carrier may also contain a means for detection such as labeled antigen or enzyme substrates or the like.

Nucleotide sequences that are complementary to the canine IgA encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other canine IgA antisense oligonucleotide mimetics. canine IgA antisense molecules may be introduced into cells by microinjection, liposome encapsulation or by expression from vectors harboring the antisense sequence. Canine IgA antisense therapy may be particularly useful for the treatment of diseases where it is beneficial to reduce canine IgA activity.

Pharmaceutically useful compositions comprising canine IgA DNA, canine IgA RNA, or canine IgA protein, or modulators of canine IgA activity, may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose canine IgA related disorders. The effective amount may vary according to a variety of factors such as the animal's condition, weight, sex and age. Other factors include the mode of administration.

The pharmaceutical compositions may be provided to the animal by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the canine IgA or its activity while minimizing any potential toxicity. In addition, co-administration or sequential administration of other agents may be desirable.

The present invention also has the objective of providing suitable topical, oral, systemic and parenteral pharmaceutical formulations for use in the methods of treatment of the present invention. The compositions containing compounds identified according to this invention as the active ingredient for use in the modulation of canine IgA can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a canine IgA modulating agent.

The daily dosage of the products may be varied over a wide range. Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the animal, the severity of the condition to be treated, and the particular compound thereof employed. A veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carder materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxy-ethylaspartamidephenol, or polyethyl-eneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Genomic Cloning

A canine liver genomic DNA bactreriophage library was purchased from Clontech Inc. and 1×10⁶ individual plaques were screened with a 4.3 kb XhoI-EcoRI fragment containing the entire human IgA constant region gene (Kirsch et. al.) essentially as described in Hieter, P., et al., 1981, Nature. 294: 536–540 and Gazdar, A., et al., 1986, Blood. 67: 1542–1549. Filters were hybridized overnight at 42° C. in a 10% Dextran Sulfate, 4x SSC, 50% formamide, 0.8% Denhardt's Tris buffered solution. After hybridization, filters were washed with 2x SSC, 0.1% SDS at room temperature for 30 minutes, 1x SSC, 0.1% SDS at room temperature for 30 minutes and 1x SSC, 0.1% SDS at 42° C. for 30 minutes. Five positive bactefiophage were plaque purified, and large scale lysates were prepared. Restriction mapping of positive bacteriophage clones were performed according to manufacturer's suggested conditions with the restriction enzymes indicated. Regions of the clones containing the canine IgA constant region were identified using the human IgA constant region probe described above.

This clone was selected for further characterization. Restriction mapping revealed that the area of homology to the human IgA constant region probe resided on two SstI fragments 0.8 and 1.2 kb in size. These fragments were subcloned independently and the regions sharing homology with the human IgA constant region were analyzed by DNA sequencing. The sequence analysis demonstrated that the canine IgA constant region gene is encoded in three exons spread out over approximately 1.5 kb of DNA. This genomic structure is consistent with the previously determined genomic structure of IgA genes from other species.

EXAMPLE 2

Nucleotide Sequence Analysis

The DNA sequence of relevant regions of the canine IgA constant region genes was determined by the "dideoxy" chain termination method using the USB Sequenase DNA sequencing kit. Synthetic oligonucleotides used as sequencing primers were synthesized on an ABI 381 synthesizer or purchased from Stratagene. Nucleic acid alignments ad translations were done using the University of Wisconsin Sequence analysis software package (Devereux, J., P. Haeverli, and O. Smithies. 1984. Nuc. Acid. Res. 12: 387–395).

EXAMPLE 3

Cloning of of Canine IgA for Expression of the Canine IgA Polypeptide in other Host Cell Systems a) Cloning of Canine IgA cDNA into a Bacterial Expression Vector.

Recombinant Canine IgA is produced in a bacterium such as E. coli following the insertion of the optimal canine IgA cDNA sequence into expression vectors designed to direct the expression of heterologous proteins. These vectors are constructed such that recombinant canine IgA is synthesized alone or as a fusion protein for subsequent manipulation. Expression may be controlled such that recombinant canine IgA is recovered as a soluble protein or within insoluble inclusion bodies. Vectors such as pBR322, pSKF, pUR, pATH, pGEX, pT7-5, pT7-6, pT7-7, pET, pIBI (IBI), pSP6/T7-19 (Gibco/BRL), pBluescript II (Stratagene), pTZ18R, pTZ19R (USB), pSE420 (Invitrogen) or the like are suitable for these purposes.

b) Cloning of Canine IgA cDNA into a Yeast Expression Vector

Recombinant Canine IgA is produced in a yeast such as *Saccharomyces cerevisiae* following the insertion of the optimal canine IgA cDNA cistron into expression vectors designed to direct the intracellular or extracellular expression of heterologous proteins. In the case of intracellular expression, vectors such as EmBLyex4 or the like are ligated to the canine IgA cistron (Rinas, U. et al., Biotechnology 8: 543–545 (1990); Horowitz B. et al., J. Biol. Chem. 265: 4189–4192 (1989)). For extracellular expression, the canine IgA cistron is ligated into yeast expression vectors which fuse a secretion signal (a yeast or mammalian peptide) to the amino terminus of the canine IgA protein (Jacobson, M. A., Gene 85: 511–516 (1989); Riett L. and Bellon N. Biochem. 28: 2941–2949 (1989)).

c) Cloning of Canine IgA cDNA into a Viral Expression Vector

Recombinant canine IgA is produced in mammalian host cells, such as HeLa S3 cells, after infection with vaccinia virus containing the canine IgA cDNA sequence. To produce canine IgA:vaccinia virus, the canine IgA cDNA is first ligated into a transfer vector, such as pSC11, pTKgptFls, pMJ601 or other suitable vector, then transferred to vaccinia virus by homologous recombination. After plaque purification and virus amplification, canine IgA:vaccinia virus is used to infect mammalian host cells and produce recombinant canine IgA protein.

EXAMPLE 4

Process for the Production of a Recombinant Canine IgA polypeptide

Recombinant canine IgA is produced by a) transforming a host cell with DNA encoding canine IgA protein to produce a recombinant host cell;

b) culturing the recombinant host cell under conditions which allow the production of canine IgA; and c) recovering the canine IgA.

The recombinant canine IgA is purified and characterized by standard methods.

EXAMPLE 5

Compounds that modulate canine IgA activity may be detected by a variety of methods. A method of identifying compounds that affect canine IgA comprises:

(a) mixing a test compound with a solution containing canine IgA to form a mixture;

(b) measuring canine IgA activity in the mixture; and (c) comparing the canine IgA activity of the mixture to a standard.

Compounds that modulate canine IgA activity may be formulated into pharmaceutical compositions. Such pharmaceutical compositions may be useful for treating diseases or conditions that are characterized by altered canine IgA activity. Examples of such diseases wherein the canine IgA activity is altered include allergic reactions.

EXAMPLE 6

DNA which is structurally related to DNA encoding canine IgA is detected with a probe. A suitable probe may be derived from DNA having all or a portion of the nucleotide sequence of FIG. 1, RNA encoded by DNA having all or a portion of the nucleotide sequence of FIG. 1, degenerate oligonucleotides derived from a portion of the amino acid sequence of FIG. 1 or an antibody directed against canine IgA.

EXAMPLE 7

A kit for the detection and characterization of DNA or RNA encoding canine IgA or canine IgA is prepared by conventional methods. The kit may contain DNA encoding canine IgA, recombinant canine IgA, RNA corresponding to the DNA encoding canine IgA or antibodies to canine IgA. The kit may be used to characterize test samples, such as forensic samples, taxonomic samples or epidemiological samples.

EXAMPLE 8

Use of Mutagenized Canine IgA

DNA encoding canine IgA is mutagenized using standard methods to produce an altered canine IgA gene. Host cells are transformed with the altered canine IgA to produce altered canine IgA protein. The altered canine IgA protein may be isolated, purified and used to characterize the function of canine IgA protein.

EXAMPLE 9

Preparation of Immunogenic Compositions

Purified recombinant canine IgA are formulated according to known methods, such as by the admixture of a pharmaceutically acceptable carder or a vaccine adjuvant.

The amount of canine IgA per formulation may vary according to a variety of factors, including but not limited to the animal's condition, weight, age and sex. Such formulations are administered to an animal in amounts sufficient to induce an immune response in the animal. Administration of the recombinant canine IgA formulation may be by a variety of routes, including but not limited to oral, subcutaneous, topical, mucosal and intramuscular.

EXAMPLE 10

Preparation of Antibodies to Canine IgA

Purified recombinant canine IgA is used to generate antibodies. The term "antibody" as used herein includes both polyclonal and monoclonal antibodies as well as fragments thereof, such as Fv, Fab and F(ab)2 fragments that are capable of binding antigen or hapten. The antibodies are used in a variety of ways, including but not limited to the purification of recombinant canine IgA, the purification of native canine IgA, and kits. Kits would comprise a compartmentalized carrier suitable to hold in close confinement at least one container. The carrier would further comprise reagents such as the anti-canine IgA antibody or the recombinant canine IgA suitable for detecting canine IgA or fragments of canine IgA or antibodies to canine IgA. The carrier may also contain means for detection such as labeled antigen or enzyme substrates or the like. The antibodies or canine IgA or kits are useful for a variety of purposes, including but not limited to forensic analyses and epidemiological studies.

---

What is claimed is:

1. A DNA molecule comprising of a nucleotide sequence of SEQ. ID. NO.:1.

2. An expression vector comprising the DNA molecule of claim 1.

3. A recombinant cell transformed with the vector of claim 2.

4. A process for expression of recombinant canine immunoglobulin A, comprising culturing the cells of claim 3 under conditions which allow expression of canine immunoglobulin A.

* * * * *